United States Patent
Wada et al.

(10) Patent No.: US 9,308,290 B2
(45) Date of Patent: Apr. 12, 2016

(54) WATER-ABSORBING AGENT, MANUFACTURE METHOD THEREOF, AND ABSORBENT AND ABSORBENT ARTICLE MADE THEREFROM

(71) Applicants: Katsuyuki Wada, Himeji (JP); Makoto Nagasawa, Himeji (JP); Kunihiko Ishizaki, Osaka (JP)

(72) Inventors: Katsuyuki Wada, Himeji (JP); Makoto Nagasawa, Himeji (JP); Kunihiko Ishizaki, Osaka (JP)

(73) Assignee: NIPPON SHOKUBAI CO., LTD., Osaka-Shi, Osaka (JP)

( * ) Notice: Subject to any disclaimer, the term of this patent is extended or adjusted under 35 U.S.C. 154(b) by 78 days.

(21) Appl. No.: 14/029,878

(22) Filed: Sep. 18, 2013

(65) Prior Publication Data

US 2014/0058346 A1    Feb. 27, 2014

Related U.S. Application Data

(63) Continuation of application No. 10/581,603, filed as application No. PCT/JP2004/018871 on Dec. 10, 2004, now abandoned.

(30) Foreign Application Priority Data

Dec. 12, 2003   (JP) .................................. 2003-415117

(51) Int. Cl.
*A61F 13/53*   (2006.01)
*A61L 15/24*   (2006.01)
(Continued)

(52) U.S. Cl.
CPC .............. *A61L 15/24* (2013.01); *A61F 13/535* (2013.01); *A61L 15/42* (2013.01); *A61L 15/60* (2013.01);
(Continued)

(58) Field of Classification Search
CPC .............. A61F 13/15203; A61F 13/53; A61F 2013/15447; A61F 2013/15463; A61F 2013/15471; A61F 2013/530481; A61F 2013/530489; A61F 2013/530569; A61F 2013/530591; A61F 2013/530671; A61F 2013/530708; A61F 2013/530737; A61F 2013/530751; A61F 2013/530766; A61F 2013/530773; A61L 15/18; A61L 15/24; A61L 15/26; A61L 15/60
See application file for complete search history.

(56) References Cited

U.S. PATENT DOCUMENTS

| 4,093,776 A | 6/1978 | Aoki et al. |
| 4,286,082 A | 8/1981 | Tsubakimoto et al. |

(Continued)

FOREIGN PATENT DOCUMENTS

| DE | 4020780 C1 | 8/1991 |
| DE | 19543366 A1 | 5/1997 |

(Continued)

OTHER PUBLICATIONS

International Search Report for PCT/JP2004/18871 dated Mar. 22, 2005.

(Continued)

*Primary Examiner* — Lynne Anderson
(74) *Attorney, Agent, or Firm* — Nixon & Vanderhye, PC (57) ABSTRACT

To improve the heat retention by diapers and other absorbents, a heat retention indicator 1 of a water-absorbing resin which is defined in the present invention needs be 3.0° C./min or less and also that particular requirements need be met to satisfy this condition. If the requirements are met, a water-absorbing resin, absorbent, and absorbent article can be provided which has a heat retention indicator 1 of 0 to 3.0° C./min or less and which exhibits excellent heat retention and absorption.

12 Claims, 1 Drawing Sheet

(51) Int. Cl.
*A61L 15/42* (2006.01)
*A61L 15/60* (2006.01)
*A61F 13/535* (2006.01)
*A61F 13/15* (2006.01)

(52) U.S. Cl.
CPC ............ *A61F 2013/15463* (2013.01); *A61F 2013/530569* (2013.01); *A61F 2013/530591* (2013.01); *A61F 2013/530708* (2013.01); *A61F 2013/530737* (2013.01); *A61F 2013/530766* (2013.01)

(56) References Cited

U.S. PATENT DOCUMENTS

| | | | |
|---|---|---|---|
| 4,367,323 | A | 1/1983 | Kitamura et al. |
| 4,446,261 | A | 5/1984 | Yamasaki et al. |
| 4,625,001 | A | 11/1986 | Tsubakimoto et al. |
| 4,683,274 | A | 7/1987 | Nakamura et al. |
| 4,873,299 | A | 10/1989 | Nowakowsky et al. |
| 4,973,632 | A | 11/1990 | Nagasuna et al. |
| 4,985,518 | A | 1/1991 | Alexander et al. |
| 5,026,800 | A | 6/1991 | Kimura et al. |
| 5,051,259 | A | 9/1991 | Olsen et al. |
| 5,124,416 | A | 6/1992 | Haruna et al. |
| 5,145,906 | A | 9/1992 | Chambers et al. |
| 5,147,343 | A | 9/1992 | Kellenberger |
| 5,149,335 | A | 9/1992 | Kellenberger et al. |
| 5,244,735 | A | 9/1993 | Kimura et al. |
| 5,250,640 | A | 10/1993 | Irie et al. |
| 5,264,495 | A | 11/1993 | Irie et al. |
| 5,380,808 | A | 1/1995 | Sumiya et al. |
| 5,409,771 | A | 4/1995 | Dahmen et al. |
| 5,599,335 | A | 2/1997 | Goldman et al. |
| 5,684,106 | A | 11/1997 | Johnson et al. |
| 5,797,893 | A | 8/1998 | Wada et al. |
| 6,087,002 | A | 7/2000 | Kimura et al. |
| 6,087,450 | A | 7/2000 | Breitbach et al. |
| 6,143,821 | A | 11/2000 | Houben |
| 6,222,091 | B1 | 4/2001 | Beihoffer et al. |
| 6,224,961 | B1 | 5/2001 | Hseuh et al. |
| 6,297,335 | B1 | 10/2001 | Funk et al. |
| 6,376,618 | B1 | 4/2002 | Mitchell et al. |
| 6,514,615 | B1 | 2/2003 | Sun et al. |
| 6,586,549 | B1 | 7/2003 | Hatsuda et al. |
| 6,617,489 | B2 | 9/2003 | Wada et al. |
| 2002/0128618 | A1 | 9/2002 | Frenz et al. |
| 2002/0165288 | A1 | 11/2002 | Frenz et al. |
| 2003/0069359 | A1 | 4/2003 | Torii et al. |
| 2006/0229413 | A1 | 10/2006 | Torii et al. |

FOREIGN PATENT DOCUMENTS

| | | |
|---|---|---|
| EP | 0 532 002 | 3/1993 |
| EP | 0 615 736 | 9/1994 |
| EP | 0 761 191 | 3/1997 |
| EP | 0 811 636 | 12/1997 |
| EP | 0 882 502 | 12/1998 |
| EP | 0 922 717 | 6/1999 |
| EP | 0947184 A1 | 10/1999 |
| EP | 0 955 086 | 11/1999 |
| JP | H09-309916 | 12/1997 |
| JP | 11-140194 | 5/1999 |
| JP | 2003-62460 | 3/2003 |
| JP | 2003-508202 | 3/2003 |
| JP | 2003-105092 | 4/2003 |
| JP | 2003-137922 | 5/2003 |
| JP | 2003-313446 | 11/2003 |
| JP | 2004-217911 | 8/2004 |
| JP | 2004-261796 | 9/2004 |
| JP | 2004-261797 | 9/2004 |
| WO | 02/053198 A1 | 7/2002 |
| WO | 02/100451 A2 | 12/2002 |
| WO | 2004/099265 A1 | 11/2004 |

OTHER PUBLICATIONS

European Patent Application No. 04807229.2, mailing date of the Notice of Opposition, Nov. 3, 2011.
Office Action of U.S. Appl. No. 10/581,603 dated Jul. 31, 2013.
Office Action of U.S. Appl. No. 10/581,603 dated Nov. 15, 2010.
Office Action of U.S. Appl. No. 10/581,603 dated Jun. 15, 2010.
Office Action of U.S. Appl. No. 10/581,603 dated Jan. 29, 2010.
Office Action of U.S. Appl. No. 10/581,603 dated Jul. 6, 2009.
Office Action of U.S. Appl. No. 10/581,603 dated Mar. 5, 2009.
Communication and Letter issued Feb. 3, 2015 against Corresponding European Application No. 04807229.2 (with translation).
Official Communication issued May 8, 2015 in European Patent Application No. 04 807 229.2 (with translation).
Official Communication issued Sep. 23, 2015 in European Patent Application No. 04 807 229 (with translation).

WATER-ABSORBING AGENT, MANUFACTURE METHOD THEREOF, AND ABSORBENT AND ABSORBENT ARTICLE MADE THEREFROM

This application is a continuation of application Ser. No. 10/581,603, filed on Jun. 5, 2006 which is the US national phase of international application PCT/JP2004/018871, filed Dec. 10, 2004, which designated the U.S. and claims priority of JP 2003-415117, dated Dec. 12, 2003, the entire contents of each of which are hereby incorporated by reference.

TECHNICAL FIELD

The present invention, relates to water-absorbing agents primarily composed of water-absorbing resin suitably used in, for example, paper diapers (disposable diapers), sanitary napkins, so-called incontinence pads, and other hygiene materials. More specifically, the invention relates to water-absorbing agents (resins), as well as their manufacturing methods and uses, of which crosslinked: have a heat retention indicator 1 of 3.0 or less, a centrifuge retention capacity (CRC) of 34 g/g or less in a 0.90 wt. % aqueous solution of sodium chloride, and an absorbency of 30 g/g or less in a 0.90 wt. % aqueous solution of sodium chloride against a pressure of 2.0 kPa; contain 60 wt. % or more particles measuring 600 μm to 300 μm in diameter and 3 wt. % or less particles measuring less than 150 μm in diameter; and have a mass-average (weight-average) particle diameter of 400 μm to 600 μm, a standard deviation of logarithm ($\sigma\zeta$) of particle size distribution of 0.250 to 0.400, and a saline flow conductivity (SFC) of less than $20 \times 10^{-7}$ cm$^3$ sec/g for a 0.69 wt. % aqueous solution of sodium chloride.

BACKGROUND ART

Water-absorbing resins are popularly used as water-absorbing agent absorbing body fluids (urine, blood, etc.) and the like, providing major components for paper diapers, sanitary napkins, incontinence pads, and other hygiene materials.

Recent years have seen development of deodorizing or otherwise value-added water-absorbing resins in response to increasing demands for adult disposable diapers from aging populations. Also under development are diapers which feel comfortable when worn. These diapers well fit body shape and allow no leak. These enhancements are mostly due to structural improvements of the absorbent, but partly attributable to improved performance of the water-absorbing resin.

The performance includes, for example, seepage and diffusing absorbency. Related improvements have been made in terms of centrifuge retention capacity (CRC), absorbency against pressure (AAP), gel strength, and absorption rate.

Document 1, or U.S. Pat. No. 5,147,343, discloses a porous fiber matrix and an absorbent composition made from a superabsorbent polymer dispersed in the pores in the fiber matrix. The superabsorbent polymer can absorb at least 27 ml of a 0.9 wt. % solution of sodium chloride against a pressure of 21000 dyne/cm$^2$. The absorbent composition advantageously contains a 10 wt. % to 60 wt. % superabsorbent polymer.

Document 2, or U.S. Pat. No. 5,149,335, describes an absorbent structure of a 60 wt. % to 100 wt. % superabsorbent polymer. The superabsorbent polymer is characterized by a free swell rate of less than 60 seconds and at least a 5-minutes AUL (absorption under load) of 15 g/g.

Document 3, or European patent 0532002, discloses a porous fiber matrix and an absorbent composition containing an at least 30 wt. % superabsorbent polymer. The superabsorbent polymer has a deformation under load of less than 0.60 mm and a wicking index of 10 cm or more.

Document 4, or European patent 0615736, relates to an absorbent composition containing a 30 wt. % to 100 wt. % superabsorbent polymer which has a pressure absorbency index of at least 100 and an extractable content of less than 13 wt. % (during a 16-hour extraction in a 0.9 wt. % aqueous solution of sodium chloride).

Document 5, or European patent 0761191, describes a fiber matrix and an absorbent composition containing an at least 30 wt. %, superabsorbent polymer which has a suction parameter of 700 or more.

Document 6, or U.S. Pat. No. 6,297,335, discloses an absorbent composition with a pressure absorbency index of less than 100 and a vertical absorption of at least 12 g/g against a pressure of 1922.8 Pa.

Document 7, or U.S. Pat. No. 5,599,335, discloses an absorbent composition with a saline flow conductivity (SFC) of at least about $30 \times 10^{-7}$ cm$^3$ sec/g for a 0.69 wt. % aqueous solution of sodium chloride and a performance of at least 23 g/g under a load of 0.7 psi (performance under load, or PUP).

One of obvious conditions of comfort in wearing a diaper or similar absorbent is quick absorption of urine or other body fluids after excretion. The foregoing, conventional methods focus on the water-absorption performance of the water-absorbing resin or absorbent such as the diaper. This approach alone however will fall short of providing sufficient comfort when the diaper or like absorbent is worn. Examining causes of discomfort, we have found that a "drop in temperature" of the absorbent after the diaper or like absorbent absorbs excreted urine or other body fluids, that is, the "cool feel" of the wearer, is the factor that seriously affects comfort. No conventional absorbents can prevent a drop in their temperature. Heat retention has not been considered. None of them have achieved a satisfactory level of heat retention in actual use.

Sacrificing absorption performance to give high heat retention would result in the water-absorbing resin failing to accomplish its basic goals of absorbing body fluids (urine, blood, etc.). Therefore, it is both important to give high heat retention and attain a required level of absorption performance.

As in the foregoing, a lot of improvements have been made on the absorption performance of the water-absorbing resin.

One of obvious conditions for a diaper or similar absorbent that is comfortable to wear is quick absorption of urine or other body fluids after excretion. However, many absorbents after being wet cool down (toward room temperature) with time after the absorption of a body fluid (generally at about body temperature). The cool feel is never comfortable. To put it differently, the wearer's problem, that is, discomfort, will be eased if the absorbent remains near the body temperature level for an extended period after the absorption of a body fluid.

DISCLOSURE OF INVENTION

The present invention has an objective to provide a water-absorbing agent, absorbent, and absorbent article with excellent heat retention and absorption performance, as well as a method of manufacturing the water-absorbing resin.

To achieve excellent heat retention and absorption performance with a diaper or like absorbent, the inventors have focused on the water-absorbing resin that greatly affects the performance of the absorbent.

During the course of the research, the inventors have found that the heat retention of a diaper can be enhanced by improving a particular capability of the water-absorbing resin, which has led to the completion of the invention.

Some causes of discomfort in actual use of a diaper and like absorbent are stickiness due to seeping liquid and the feel of cold gel which has absorbed liquid. Attempts have been conventionally made to reduce stickiness. In the present invention, however, the feel of cold gel, as well as stickiness, is reduced.

The aforementioned particular capability is measured by a "heat retention indicator 1" of the water-absorbing resin in the present invention. This is an absolutely novel parameter for the water-absorbing resin. The calculation of the heat retention indicator 1 will be discussed later in detail by way of examples along with related experiments. In short, the heat retention indicator 1 is a representation of a temperature change on the surface of the water-absorbing resin over a unit time after a liquid is poured into the water-absorbing resin. The unit time here is 5 to 10 minutes. The lower the heat retention indicator 1, the smaller the temperature change on the water-absorbing resin surface, and the better the heat retention.

The inventors have also found that a water-absorbing resin with a satisfactory heat retention indicator 1 value in accordance with the present invention can be prepared by controlling the centrifuge retention capacity, absorbency against pressure, and particle diameter of the water-absorbing resin in particular ranges during manufacture.

Specifically, the water-absorbing resin has a centrifuge retention capacity of 34 g/g or less in a 0.90 wt. % aqueous solution of sodium chloride and an absorbency of 30 g/g or less in a 0.90 wt. % aqueous solution of sodium chloride against a pressure of 2.0 kPa; contains 60 wt. % or more particles measuring 600 µm to 300 µm in diameter and 3 wt. % or less particles measuring less than 150 µm in diameter; and has a mass-average particle diameter of 400 µm to 600 µm, a standard deviation of logarithm (σζ) of particle size distribution of 0.250 to 0.400, and a saline flow conductivity (SFC) of less than $20 \times 10^{-7}$ cm$^3$ sec/g for a 0.69 wt. % aqueous solution of sodium chloride. It has turned out that satisfying these conditions brings down a heat retention indicator 1 (maximum temperature decrease per minute 5 to 10 minutes after 10 times swelling at 50° C.) to 3.0 or less, and creates an absorbent with excellent absorption performance and heat retention. In other words, the resultant diaper and other absorbent feel less cold after they have absorbed a body fluid (urine, blood, etc.).

A water-absorbing agent of the present invention contains a water-absorbing resin having a crosslinking structure constructed by polymerization of an unsaturated monomer component as a major component. The water-absorbing resin is surface-treated (crosslinked). Besides the water-absorbing resin, the water-absorbing agent may further contain water-insoluble inorganic fine particles where necessary. The water-absorbing resin meets the following conditions: its heat retention indicator 1 be 3.0 or less; its centrifuge retention capacity in a 0.90 wt. % aqueous solution of sodium chloride be 34 g/g or less; its absorbency in a 0.90 wt. % aqueous solution of sodium chloride against a pressure of 2.0 kPa be 30 g/g or less; it contain 60 wt. % or more particles measuring 600 µm to 300 µm in diameter and 3 wt. % or less particles measuring less than 150 µm in diameter; its mass-average particle diameter be from 400 µm to 600 µm; its standard deviation of logarithm (σζ) of particle size distribution be from 0.250 to 0.400; and its saline flow conductivity (SFC) for a 0.69 wt. % aqueous solution of sodium chloride be less than $20 \times 10^{-7}$ cm$^3$ sec/g. These are features of the water-absorbing agent of the present invention.

An absorbent in accordance with the present invention contains a water-absorbing agent in accordance with the present invention and hydrophilic fibers.

An absorbent article in accordance with the present invention contains an absorbent in accordance with the present invention, a liquid-permeable top sheet, and a liquid-impermeable back sheet.

A method of manufacturing a water-absorbing agent in accordance with the present invention is a method of manufacturing a water-absorbing agent containing a water-absorbing resin having a crosslinking structure constructed by polymerization of an unsaturated monomer component as a major component. The method involves: the polymerization step of polymerizing a monomer component containing an acid-group-containing unsaturated monomer as a major component to prepare a water-absorbing resin; the step of surface-treating the water-absorbing resin; and where necessary, the step of adding inorganic fine particles. The water-absorbing agent obtained in the steps meets the following conditions: its heat retention indicator 1 be 3.0 or less; its centrifuge retention capacity in a 0.90 wt. % aqueous solution of sodium chloride be 34 g/g or less; its absorbency in a 0.90 wt. % aqueous solution of sodium chloride against a pressure of 2.0 kPa be of 30 g/g or less; it contain 60 wt. % or more particles measuring 600 µm to 300 µm in diameter and 3 wt. % or less particles measuring less than 150 µm in diameter; its mass-average particle diameter be 400 µm to 600 µm; and its standard deviation of logarithm (σζ) of particle size distribution be 0.250 to 0.400. Further, the water-absorbing agent obtained in the steps has a saline flow conductivity (SFC) of less than $20 \times 10^{-7}$ cm$^3$ sec/g for a 0.69 wt. % aqueous solution of sodium chloride. These are features of the method.

Additional objects, advantages and novel features of the invention will be set forth in part in the description which follows, and in part will become apparent to those skilled in the art upon examination of the following or may be learned by practice of the invention.

BEST MODE FOR CARRYING OUT THE INVENTION

The inventors have focused on good heat retention, not to mention good water absorption, as properties needed with the diaper and like absorbent (absorbent article), with a purpose of developing an absorbent which gives the wearer less of the uncomfortable, cold feel which results from a post-liquid-absorption gel temperature decrease. Accordingly, the inventors have paid special attention to the water-absorbing agent which severely affects the performance of the absorbent. The inventors have found that the heat retention of the absorbent can be improved through the particular capability of the water-absorbing agent, which has led to the completion of the invention. That is, the inventors have found that the heat retention (comfort) of the absorbent (diaper) in actual use is well related with the specific parameter of the water-absorbing agent, which has led to the completion of the invention.

In the present invention, the particular capability is referred to as the heat retention indicator 1 of the water-absorbing agent. This is an absolutely novel parameter for the water-absorbing agent (or water-absorbing resin) which cannot be found in prior art. The calculation of the heat retention indicator 1 will be discussed later in detail by way of examples along with related experiments. In short, the heat retention indicator 1 is a representation of a temperature change on the surface of the water-absorbing agent (or water-absorbing resin) over a unit time after a liquid is poured into the water-absorbing agent (or water-absorbing resin). The unit time here is 5 to 10 minutes. The lower the heat retention indicator 1, the smaller the temperature change on the water-absorbing resin surface, and the better the heat retention.

The inventors have discovered that the water-absorbing agent (or water-absorbing resin) comes to exhibit a satisfactory heat retention indicator 1 in accordance with the present invention through the control of the centrifuge retention capacity, absorbency against pressure, and particle diameter of the water-absorbing agent (or water-absorbing resin) in particular ranges during manufacture.

The following will describe the water-absorbing agent (or water-absorbing resin) in accordance with the present invention in detail. The scope of the present invention is nevertheless by no means limited by the description. The invention can be practiced outside the examples without departing from the spirit and scope of the invention.

First, a brief explanation will be given regarding the water-absorbing resin, water-absorbing agent, absorbent, and absorbent article in accordance with the present invention.

Water-Absorbing Resin

The water-absorbing resin in accordance with the present invention is a conventionally known water-absorbing resin. An example is a conventional, publicly known crosslinked polymer that absorbs large quantities of water (50 to 1000 times) in ion-exchanged water to produce an anionic, non-ionic, or cationic water-insoluble hydrogel.

As a water-absorbing resin, the resin must be swellable in, and insoluble to, water. The uncrosslinked, water-soluble content (water-soluble polymer) in the water-absorbing resin is preferably 0 to 30 wt. % inclusive, more preferably 0 to 25 wt. % inclusive, even more preferably 0 to 20 wt. % inclusive, and still preferably 0 to 15 wt. % inclusive. Specific features of the water-absorbing resin will be detailed later.

Water-Absorbing Agent

The water-absorbing agent in accordance with the present invention contains as a major component the aforementioned water-absorbing resin which is crosslinked on the surface (secondary crosslink). The water-absorbing resin accounts for preferably 80 wt. % or more, more preferably 90 wt % or more of the water-absorbing agent. The agent is normally in powder form. Specific features of the water-absorbing agent will be detailed later.

Needless to say, in the present invention, the water-absorbing resin per se can function as the water-absorbing agent. Therefore, in the following description, the term, water-absorbing agent, encompasses the water-absorbing resin.

Absorbent

The absorbent in accordance with the present invention is a molded article (e.g. sheet shape) which contains the aforementioned water-absorbing agent (or water-absorbing resin) and hydrophilic fibers as water-absorbing supplement.

Absorbent Article

The absorbent article in accordance with the present invention contains the aforementioned absorbent, a liquid-permeable top sheet, and a liquid-impermeable back sheet (e.g., diapers and sanitary napkins).

Next, a method of manufacturing a water-absorbing resin will be describe.

Method of Manufacturing Water-Absorbing Resin (Polymerization Step)

The water-absorbing resin in accordance with the present invention is typically prepared by polymerizing a monomer in solution form, drying the polymer where necessary, and crushing either before or after drying if necessary. Examples of such a water-absorbing resin include partially neutralized polymers of polyacrylic acid, hydrolyzed starch/acrylonitrile graft polymers, starch/acrylic acid graft polymers, saponification products of vinyl acetate/acrylic ester copolymers, hydrolyzed acrylonitrile copolymers and acrylamide copolymers, and crosslinked products of these substances; denatured products of crosslinked polyvinyl alcohols containing carboxyl groups; and crosslinked isobutylene/maleic anhydride copolymers. These water-absorbing resins may be used either alone or in any combination.

The water-absorbing resins may be used either alone or in any combination. Preferable among them are the water-absorbing resins containing acid groups and those containing carboxyl groups, either used alone or in combination. A typical major component is a polymer obtained by polymerizing and crosslinking a monomer primarily composed of an acrylic acid and/or its salt (neutralized product). Throughout this specification and accompanied set of claims, the crosslinking which takes place during the course of the polymerization and crosslinking of a monomer will be referred to as "primary crosslinking" so that it can be distinguished from the crosslinking (surface crosslinking or secondary crosslinking) which takes place during the course of the manufacture of a water-absorbing agent (will be detailed later).

Examples of such salts of acrylic acid include alkali metal salts, such as sodium, potassium, and lithium salts, of acrylic acid; ammonium salt of acrylic acid (acrylate); and amine salts of acrylic acid. The water-absorbing resin contains preferably 0 to 50 mole % acrylic acid and 100 to 50 mole % acrylate (the sum should be 100 mole %), more preferably 10 to 40 mole % acrylic acid and 90 to 60 mole % acrylate (the sum should be 100 mole %). The salt-forming neutralization of the water-absorbing resin may be performed before polymerization, that is, when the resin is still in monomer form, or during or after polymerization, that is, when the resin is already in polymer form. Combinations of these approaches may be used.

If a monomer which shows a zero or low level of neutrality is polymerized, and the resultant polymer is neutralized (acid type polymerization method), the obtained water-absorbing resin generally tends to be highly absorbent and less water-soluble content; however, it requires a lot of work, equipment, and time to uniformly neutralize individual particles of the water-absorbing resin. See Japanese unexamined patent application 10-10173 (Tokukaihei 10-10173/1998) and European unexamined patent publication 882502. Therefore, neutral polymerization is preferred.

The monomer from which the water-absorbing resin for use in the present: invention is derived may include monomers other than acrylic acid (salts) where necessary. Specific examples of such monomers include, although not limited to, anionic unsaturated monomers and their salts, such as methacrylic acid, maleic acid, vinylsulfonic acid, styrenesulfonic acid, 2-(meth)acrylamide-2-methylpropanesulfonic acid, 2-(meth)acryloylethanesulfonic acid, and 2-(meth)acryloylpropanesulfonic acid; unsaturated monomers containing non-ionic hydrophilic groups; such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl(meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, N-acryloylpyrrolidine, and N-vinyl acetoamide; and cationic unsaturated monomers, such as N,N-dimethylaminoethyl(meth)acrylate, N,N-diethylaminoethyl(meth)acrylate, N,N-dimethylaminopropyl(meth)acrylate, N,N-dimethylaminopropyl(meth) acrylamide, and their quaternary salts. These monomers may be used alone or, two or more of them may be mixed for use in any suitable combination.

If a monomer other than acrylic acid (salts) is used in the present invention, that monomer is preferably 0 to 30 mole % inclusive, more preferably 0 to 10 mole % inclusive, of the total of the acrylic acid and its salts which are the major components. Using a monomer other than the acrylic acid (salts) at this ratio further improves the absorption property of the finished water-absorbing resin (or water-absorbing agent) and reduces the production cost of the water-absorbing resin (or water-absorbing agent).

The monomer from which the water-absorbing resin for use in the present invention can be polymerized by bulk polymerization or precipitation polymerization. Considering performance, ease in control, and absorption of the swollen gel, however, reverse suspension polymerization and aqueous solution polymerization where the monomer is dissolved in water are preferred.

If the monomer is dissolved, in water, the monomer concentration in the aqueous solution (hereinafter, the monomer aqueous solution) is determined according to the temperature of the aqueous solution and the monomer. The concentration is preferably 10 to 70 wt. %, more preferably 20 to 60 wt. %. These figures are however not meant to be limiting in any particular manner. To carry out aqueous solution polymerization, solvents other than water may be used together with water where necessary. The kinds of solvents used are not limited in any particular manner.

In reverse suspension polymerization, a monomer aqueous solution is suspended in a hydrophobic organic solvent for polymerization. The method is described, for example, in U.S. Pat. Nos. 4,093,776, 4,367,323, 4,446,261, 4,683,274, and 5,244,735. In aqueous solution polymerization, a monomer aqueous solution is polymerized without using a dispersing solvent. The method is described, for example, in U.S. Pat. Nos. 4,625,001, 4,873,299, 4,286,082, 4,973,632, 4,985, 518, 5,124,416, 5,250,640, 5,264,495, 5,145,906, and 5,380, 808 and European patents 0811636, 0955086, and 0922717. The monomer components and initiators disclosed in the patents are applicable to the present invention.

Aqueous solution polymerization may be performed, for example, in a double-arm kneader which crushes produced water-containing gel while the polymerization of a monomer aqueous solution is in progress. An alternative is to place the monomer aqueous solution in a predetermined container or on conveyor belt and crush the polymerized gel with a meat chopper.

To initiate the polymerization, a radical polymerization initiator or a polymerization photoinitiator may be used. Examples of the former include potassium persulfate, ammonium persulfate, sodium persulfate, t-butylhydroperoxide, hydrogen peroxide, and 2,2'-azobis(2-amidinopropane)dihydrochloride. An example of the latter is 2-hydroxy-2-methyl-1-phenyl-propane-1-on.

Further, a reducing agent may be used together to accelerate the dicomposition of the polymerization initiator. The combination offers a redox initiator. Examples of such a reducing agent include, although not limited to, (bi)sulfurous acid (salts), such as sodium sulfite and sodium hydrogen sulfite; reducing metals (salts), such as L-ascorbic acid (salts) and ferrous salt; and amines.

The polymerization initiator is used typically at 0.001 to 2 mole %, preferably at 0.01 to 0.1 mole %. If the polymerization initiator is used at less than 0.001 mole %, an increased amount of the unreacted monomer remains, undesirably leaving an increased amount of residual monomer in the produced water-absorbing resin and water-absorbing agent. In contrast, If the polymerization initiator is used in excess of 2 mole %, the produced water-absorbing resin and water-absorbing agent has a more water-soluble content. This is undesirable in some cases.

Another way of initiating a polymerization reaction is to irradiate an high energy beam, such as a radiation beam, electron beam, or ultraviolet beam, to the reaction system. Further, the polymerization initiator may be used together. The reaction temperature for the polymerization reaction, although not limited in any particular manner, is preferably from 15 to 130° C., more preferably from 20 to 120° C. The reaction time, polymerization pressure, and other conditions, since not limited in any particular manner, should be determined suitably according to the kinds of monomer and polymerization initiator, the reaction temperature, and other factors.

The water-absorbing resin may be of a self-crosslinking type which does not require the use of a crosslinking agent. Preferably, however, the water-absorbing resin involves a copolymerized or reacted crosslinking agent (internal crosslinking agent for the water-absorbing resin) that contains multiple unsaturated polymerizing groups or reactive groups per molecule.

Specific examples of such an internal crosslinking agent include N,N'-methylene bis(meth)acrylamide, (poly)ethylene glycol di(meth)acrylate, (poly)propylene glycol di(meth) acrylate, trimethylolpropane tri(meth)acrylate, glycerine tri (meth)acrylate, glycerine acrylate methacrylate, ethylene oxide denatured trimethylolpropane tri(meth)acrylate, pentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerine, pentaerythritol, ethylenediamine, ethylene carbonate, propylene carbonate, polyethyleneimine, and glycidyl (meth)acrylate.

These internal crosslinking agents may be used alone or, two or more of them may be mixed for use in any suitable combination. The internal crosslinking agent may be added to the reaction system in a single batch or in multiple batches. Considering the absorption property of the final water-absorbing resin and water-absorbing agent and other factors, it is preferable to use a compound containing multiple unsaturated polymerizing groups during polymerization if at least one or more types of internal crosslinking agents are used.

The internal crosslinking agent is used preferably at 0.001 to 2 mole % relative to the monomer, more preferably at 0.005 to 0.5 mole %, even more preferably at 0.01 to 0.2 mole %. If the internal crosslinking agent is used at less than 0.001 mole % or more than 2 mole %, the resultant absorption property may be insufficient.

To introduce a crosslinking structure inside the polymer using the internal crosslinking agent, the internal crosslinking agent should added to the reaction system before, during, or after the polymerization of the monomer. Alternatively, the agent may be added after neutralization.

In the polymerization, following substances may be added to the reaction system: 0 to 50 wt. % of hydrophilic polymers, preferably 0 to 10 wt. % (relative to the monomer), such as starch, cellulose, derivatives of starch and cellulose, polyvinyl alcohol, polyacrylic acid (polyacrylate), and crosslinked products of polyacrylic acid (salts); 0 to 10 wt. %, preferably 0 to 1 wt. % of various foaming agents, such as (hydrogen) carbonate, carbon dioxide, azo compounds, and inactive organic solvents; 0 to 10 wt. % of various surfactants; 0 to 10 wt. % of chelating agents; and 0 to 10 wt. % of chain transfer agents, such as hypophosphorous acid (hypophosphite).

If the crosslinked polymer is obtained by aqueous solution polymerization and in gel form, that is, a crosslinked, water-containing gel polymer, the crosslinked polymer is dried as necessary and normally crushed before and/or after the drying to obtain the water-absorbing resin. The drying is done typically at 80° C. to 250° C., preferably at 100° C. to 220° C., more preferably at 120° C. to 200° C. The drying time is determined according to the surface area and water ratio of the polymer, as well as the drier type, so as to achieve the target water content ratio.

The neutrality ratio of the water-absorbing resin for use in the present invention is the ratio (mole %) of the neutralized acid group (i.e., salt) to the entire acid group, and given by the expression: Neutrality Ratio=Neutralized Acid Group (Salt)/(Unneutralized Acid Group+Neutralized Acid Group (Salt)). The neutrality ratio, although not limited in any particular manner, is preferably from 30 to 90 mole %, more preferably from 50 to 80 mole %, even more preferably from 60 to 75 mole %, to sufficiently deliver the advantage of the present invention.

The resin is dried at 180° C. for 3 hours to calculate a weight reduction, or the water content. The water content ratio, although not limited in any particular manner, is preferably from 0.1 to 50 wt. %, more preferably from 0.2 to 30 wt. %, even more preferably from 0.3 to 15 wt. %, yet more preferably from 0.5 to 10 wt. %, when the physical properties of the obtained water-absorbing agent is considered. At these water content ratios, the resin is in powder form and its mass-average particle diameter is preferably about 100 to 1000 μm.

It is difficult to reduce the water ratio of the water-absorbing resin to zero. Therefore, in this specification, the "water-absorbing resin (powder)" encompasses both a completely dry water-absorbing resin and a water-absorbing resin which, although containing a small quantity of water (for example, 0.3 to 15 wt. %, preferably 0.5 to 1.0 wt. %), can be handled in powder form.

The physical properties under consideration in the Specification of a commercially available water-absorbing resin (or water-absorbing agent), which may or may not come in diapers, are measured after the resin is, for example, dried to reduce the water content ratio to 10 wt. % or less, preferably 5±2 wt. %. The drying that reduces the water ratio is preferably done under reduced pressure. However, the conditions of the drying are not limited in any particular manner, provided that the water-absorbing resin (or water-absorbing agent) does not decompose or, change its nature.

The water-absorbing resin compatible with the manufacturing method in accordance with the present invention is, for example, a water-absorbing resin in particle form. The water-absorbing resin particles used may measure in excess of 1000 μm in mass-average particle diameter when they are still in gel form straight from polymerization reaction, before undergoing a dry and pulverize process. However, the resin particles are normally dried, pulverized, and classified for a diameter suitable for usage.

The water-absorbing resin particles (powder) prepared in this manner may take any shape which is not limited in any particular manner. They may be spherical, pulverized, or irregular. Preferred for use is an irregularly pulverized shape given by a pulverization step.

The bulk specific gravity (defined in JIS K-3362) of the resin particles is preferably from 0.40 to 0.80 g/ml, more preferably from 0.50 to 0.75 g/ml, even more preferably from 0.60 to 0.73 g/ml, so as to sufficiently deliver the advantage of the present invention.

The water-absorbing resin prepared by the aforementioned method exhibits a typical saturated centrifuge retention capacity of about 10 to 100 g/g in physiological saline. The absorption and other physical properties are adjusted suitably for usage.

Next, the method of manufacturing of the water-absorbing agent will be described. As mentioned earlier, the water-absorbing resin per se can function as the water-absorbing agent. Therefore, when the water-absorbing agent is nothing but the water-absorbing resin per se, the water-absorbing agent is manufactured by the method described in the foregoing.

Surface Treatment of Water-Absorbing Resin (Surface Crosslinking Step).

The water-absorbing agent for use in the present invention is prepared by further crosslinking the water-absorbing resin on the surface (secondary crosslinking). Surface treatment in the present invention refers to subjecting the surface of a water-absorbing resin to secondary crosslinking. Surface treatment means the same as surface crosslinking treatment.

Various crosslinking agents are available to crosslink the surface (surface crosslinking agents). Preferred examples in view of improvements in the physical properties of the resultant water-absorbing agent include, but not limited to, polyhydric alcohol compounds, epoxy compounds, polyamine compounds and their condensates with haloepoxy compounds, oxazoline compounds, mono, di, or polyoxazolidinone compounds, polyvalent metallic compounds, and alkylene carbonate compounds.

The surface crosslinking agent for use in the present invention is not limited in any particular manner. Among others, those described in U.S. Pat. Nos. 6,228,930, 6,071,976, and 6,254,990 can be used. Specific examples are polyhydric alcohol compounds, such as mono, di, tri, tetra and polyethylene glycols, monopropylene glycol, 1,3-propanediol, dipropylene glycol, 2,3,4-trimethyl-1,3-pentanediol, polypropylene glycol, glycerine, polyglycerine, 2-butene-1,4-diol, 1,4-butanediol, 1,3-butanediol, 1,5-pentanediol, 1,6-hexanediol, and 1,2-cyclohexanedimethanol; epoxy compounds, such as ethylene glycol diglycidyl ether and glycidol; polyamine compounds, such as ethylenediamine, diethylenetriamine, triethylenetetramine, tetraethylenepentamine, pentaethylenehexamine, polyethyleneimine, and polyamide polyamine; haloepoxy compounds, such as epichlorohydrin, epibromohydrin, and α-methylepichlorohydrin; condensates of the polyamine compounds and the haloepoxy compounds; oxazolidinone compounds such as 2-oxazolidinone; cyclic ureas, such as ethylene urea; and alkylene carbonate compounds such as ethylene carbonate. These surface crosslinking agents may be used either alone or in any combination. To sufficiently deliver the advantage of the present invention, it is preferable if a polyhydric alcohol is used in the surface crosslinking agent. The polyhydric alcohol contains preferably 2 to 10 carbons per molecule, more preferably 3 to 8 carbons per molecule.

Depending on the compounds used and their combinations, the he surface crosslinking agent is used preferably at 0.001 to 10 wt. % relative to the water-absorbing resin, more preferably at 0.01 to 5 wt. %.

If surface crosslinking is done in the present invention, it is preferable to use water. Depending on the water ratio of the water-absorbing resin used, water is used preferably at 0.5 to 20 wt. % relative to the water-absorbing resin, more preferably at 0.5 to 10 wt. %. A hydrophilic organic solvent may be used in place of or together with water.

Specific examples of such a hydrophilic solvent include lower alcohols, such as methyl alcohol, ethyl alcohol, n-propyl alcohol, isopropyl alcohol, n-butyl alcohol, isobutyl alcohol, and t-butyl alcohol; ketones, such as acetone; ethers, such as dioxane, tetrahydrofuran, and alkoxypolyethylene glycol; amides, such as N,N-dimethylformamide; and sulfoxides, such as dimethyl sulfoxide. The hydrophilic organic solvent is used preferably at 0 to 10 wt. % relative to the water-absorbing resin, more preferably at 0 to 5 wt. %, even more preferably at 0 to 3 wt. %.

If surface crosslinking is done in the present invention, the surface crosslinking agent is mixed first with water and/or the hydrophilic organic solvent. The aqueous solution is then preferably sprayed or dropped to blend with the water-absorbing resin. Spraying is the preferred method of the two. The sprayed liquid drops measure preferably 0.1 to 300 μm in average particle diameter, more preferably 0.1 to 200 μm. When mixing the surface crosslinking agent with water and/or the hydrophilic organic solvent, water-insoluble fine powder and a surfactant may coexist provided that these substances do not negatively affect the advantage of the present invention.

The water-absorbing resin after being mixed with the surface crosslinking agent is preferably heated. The resin is heated preferably at 100 to 250° C. (the temperature of a heat medium or material), more preferably at 150 to 250° C., for 1 minute to 2 hours. For example, the resin is heated at 180° C. for 0.1 to 1.5 hours or at 200° C. for 0.1 to 1 hour.

The water-absorbing agent prepared by the foregoing surface crosslinking is preferably processed into a particular particle size to sufficiently deliver the advantage of the present invention.

This particle size regulation may be done either before or after a surface treatment. We have found that regulating the water-absorbing agent used in the present invention into a particular particle size enables the present invention to achieve an excellent advantage in actual use (for example, as a gelling agent for urine in paper diapers).

Mechanism of the surface treatment and regulation for a particular particle size leading to the advantage is not known. It is however expected that the diameter and surface condition of the gel particles of the water-absorbing agent (or water-absorbing resin) after swelling are major factors involved. Differing particle diameters are expected to affect contact areas between gel particles. Small gel particle diameters result in large contact areas, which in turn leads to low heat retention. Large gel particle diameters result in small contact areas, which in turn leads to high heat retention. The surface condition of the gel particles after surface treatment is expected to show strong hydrophobicity. Small contact areas between gel particles are expected to lead to high heat retention. Surprisingly, the surface treatment and regulation for a particular particle size in accordance with the present invention produce a synergistic effect: the surface treatment and regulation achieves far better heat retention than either the surface treatment or the regulation for a particular particle size alone. The above explanation is a mere assumption. Whether it will ever be proved or not bears no relation to the rights granted upon the present invention and by no means limit the scope and effects of the invention.

The water-absorbing resin (or water-absorbing agent) is in particle or powder form. The particle size of the water-absorbing resin (or water-absorbing agent) is preferably as follows: particles measuring 850 to 600 μm in diameter account for 10 wt. % or more, but less than 40 wt. % of all particles, those measuring 600 to 300 μm in diameter account for 60 wt. % or more, and those measuring less than 150 μm in diameter account for less than 3 wt. %. If particles measuring 850 to 600 μm in diameter account for less than 10 wt. %, those measuring 600 to 300 μm account for less than 60 wt. %, or those measuring less than 150 μm account for 3 wt. % or more, the heat retention indicator 1 increases, which is not suitable to the present invention. If those measuring 850 to 600 μm account for 40 wt. % or more, absorption rates for body fluids (urine, blood, etc.) may noticeable drop, which is again not suitable.

If the mass-average particle diameter is less than 400 μm, the heat retention indicator 1 increases, which is not suitable to the present invention. Similarly, if the mass-average particle diameter is more than 600 μm, absorption rates for body fluids (urine, blood, etc.) may noticeable drop, which is again not suitable.

The standard deviation of logarithm ($\sigma\zeta$) of the particle size distribution is preferably from 0.250 to 0.400, more preferably from 0.270 to 0.380. The standard deviation of logarithm ($\sigma\zeta$) of the particle size distribution may be adjusted by, for example, agglomeration where necessary. If the standard deviation of logarithm ($\sigma\zeta$) of the particle size distribution is less than 0.250, the heat retention property improves (the heat retention indicator 1 falls). However, the production cost rises dramatically, which is not suitable. If the standard deviation of logarithm ($\sigma\zeta$) of the particle size distribution is more than 0.400, the heat retention indicator 1 rises too much, which is not suitable to the present invention.

The water-absorbing agent for use in the present invention has preferably a centrifuge retention capacity of 20 g/g to 34 g/g inclusive, more preferably 20 g/g to 32 g/g inclusive, even more preferably 20 g/g to 30 g/g inclusive, in a 0.90 wt. % aqueous solution of sodium chloride. If the centrifuge retention capacity in a 0.90 wt. % aqueous solution of sodium chloride is less than 20 g/g, the manufacture needs to have large quantities of crosslinking agents to manufacture the water-absorbing agent, which adds to the production cost. Further, the low absorption results in the water-absorbing agent absorbing insufficient amounts of liquids. When such a resin is used as an absorbent for diapers, liquids seep out in increased quantities, causing stickiness. This is not desirable. If the centrifuge retention capacity in a 0.90 wt. % aqueous solution of sodium chloride is more than 34 g/g, the gel particles, swollen from the liquid absorption by the water-absorbing againt, become physically weaker. The gel particles may deform under, for example, the weight of the wearer. The gel layer of the ater-absorbing agent decreases in volume. As a result, the present invention may fail to sufficiently deliver its advantage of an absorbent with an improved heat retention property. Liquid may leak from the absorbent.

The water-absorbing agent for use in the present invention has preferably an absorbency of 20 g/g to 30 g/g inclusive, more preferably 20 g/g to 27 g/g inclusive, in a 0.90 wt. % aqueous solution of sodium chloride against a pressure of 2.0 kPa. The diaper and like absorbent is always under, for example, the weight of the wearer when in use. If the absorbency in a 0.90 wt. % aqueous solution of sodium chloride against a pressure of 2.0 kPa is less than 20 g/g, the water-absorbing agent absorbs an insufficient quantity of liquids against pressure. Body fluids (urine, blood, etc.) may leak from the absorbent, possibly causing stickiness. This is not desirable. If the absorbency in a 0.90 wt. % aqueous solution of sodium chloride against a pressure of 2.0 kPa is as high as 30 g/g or even higher, the water-absorbing agent needs be modified, which adds to the production cost. The increased production cost however does not provide sufficient reward in actual use of the diaper use. It is therefore unnecessary to raise the absorbency in a 0.90 wt. % aqueous solution of sodium chloride against a pressure of 2.0 kPa to or beyond 30 g/g.

The water-absorbing agent for use in the present invention has preferably a saline flow conductivity (SFC) of $0 \times 10^{-7}$ $cm^3$ sec/g or more, but less than $20 \times 10^{-7}$ $cm^3$ sec/g, more preferably $0 \times 1.0^{-7}$ $cm^3$ sec/g or more, but less than $10 \times 10^{-7}$ $cm^3$ sec/g, for a 0.69 wt. % aqueous solution of sodium chloride. The permeability of the gel layer for the body fluids (urine, blood, etc.) is one of factors realizing efficient delivery of the performance of the water-absorbing agent in the absorbent. An actual absorbent in many cases contain pulp or a like hydrophilic fiber. The hydrophilic fibers has a liquid diffusing property which helps the water-absorbing agent to deliver sufficient performance. If the saline flow conductivity (SFC) for a 0.69 wt. % aqueous solution of sodium chloride is as high as $20 \times 10^{-7}$ $cm^3$ sec/g or even higher, the permeability for body fluids (urine, blood, etc.) too high. The body fluids will likely spread across the absorbent before it is absorbed by the water-absorbing agent. The wearer may feel uneasy, for example, about the possibility of body fluids leaking from the absorbent. The wearer may feel uncomfortable from actual leaking. This is not desirable with the present invention.

The water-absorbing agent for use in the present invention has preferably a heat retention indicator 1 (maximum temperature decrease per minute 5 to 10 minutes after 10 times swelling at 50° C.) of 0 to 3.0° C./min, more preferably 0 to 2.7° C./min, even more preferably 0 to 2.5° C./min, most preferably 0 to 2.2° C./min. If the heat retention indicator 1 is more than 3.0, the heat retention property is insufficient. This is in contradiction to the objective of the present invention to provide an absorbent with excellent absorption performance which alleviates the wearer's problem. The upper limit is generally preferably about 50° C.

The water-absorbing agent for use in the present invention has preferably a heat retention indicator 2 (gel surface temperature 10 minutes after 10 times swelling at 50° C.) of 20° C. or higher, more preferably 21° C. or higher, even more preferably 22° C. or higher, still more preferably 23° C. or higher, most preferably 24° C. or higher. If the heat retention indicator 2 is lower than 20° C., the heat retention property is insufficient. This is in contradiction to the objective of the present invention to provide an absorbent with excellent absorption performance which alleviates the wearer's problem.

The water-absorbing resin (or water-absorbing agent) for use in the present invention has preferably a heat retention indicator 3 (time taken by the gel surface temperature to return to 37° C. after 10 times swelling at 50° C.) of 120 seconds or longer, more preferably 130 seconds or longer, even more preferably 140 seconds or longer, still more preferably 150 seconds or longer, most preferably 160 seconds or longer. If the heat retention indicator 3 is shorter than 120 seconds, the heat retention property is insufficient. This is in contradiction to the objective of the present invention to provide an absorbent with excellent absorption performance which alleviates the wearer's problem. There is no specific upper limit. The longer, the better. Generally, even 600 seconds will be acceptable.

To deliver the maximum advantage of the present invention, it is especially preferred to use a water-absorbing agent with specific capabilities as follows: the centrifuge retention capacity in a 0.90 wt. % aqueous solution of sodium chloride is 34 g/g or less; the absorbency in a 0.90 wt. % aqueous solution of sodium chloride against a pressure of 2.0 kPa is less than 30 g/g; the saline flow conductivity (SFC) for a 0.69 wt. % aqueous solution of sodium chloride is less than $20 \times 10^{-7}$ $cm^3$ sec/g; and the heat retention indicator 1 is 3.0° C./min or less. In addition, water-insoluble inorganic fine particles, chelating agents, deodorants, cationic polymers, etc. may be added to the water-absorbing agent, where necessary, provided that the addition does not cause the aforementioned physical properties to go outside of the ranges. These substances may be added at: 0.0001 to 10 wt. %, preferably 0.0001 to 5 wt. %, relative to the water-absorbing agent. If the substances are added at less than 0.0001 wt. %, they are not effective. If they are added at more than 10 wt. %, the production cost rises, as well as create a cause of degradation of the performance of the water-absorbing agent. This is not desirable.

The water-absorbing agent of the present invention needs to give a satisfactory value for only any one of the heat retention indicators 1 to 3. The agent does so preferably for two of the heat retention indicators 1 to 3, more preferably for the heat retention indicators 1 and 2. Most preferably, the agent does so for all the heat retention indicators 1 to 3.

Manufacturing Method for Absorbent

The absorbent in accordance with the present invention is prepared by molding powder of a water-absorbing agent containing a water-absorbing resin as a major component with another given absorbent material. The absorbent may take any shape. Preferred shapes are sheet, cylinder, film, and fabric. Especially preferably, the absorbent is fabricated into a sheet shape (web shape). If the water-absorbing resin (or water-absorbing agent) can be prepared in a sheet shape, it can be used without further processing.

To deliver the advantage of the present invention, the absorbent in accordance with the present invention contains, as a major component, a water-absorbing resin (or water-absorbing agent) with a crosslinked structure constructed by the polymerization of an unsaturated monomer component and further contains hydrophilic fibers.

Those hydrophilic fibers for use in the present invention are not limited in any particular manner. Examples include crushed wood pulp, cotton linters, crosslinked cellulose fibers, rayon, cotton, wool, acetate, and vinylon. Preferably, these materials are used after being airlaid.

The absorbent is manufactured from the aforementioned water-absorbing agent and hydrophilic fibers in accordance with the present invention.

In the absorbent in accordance with the present invention, the water-absorbing resin preferably accounts for 20 to 100% wt. % (core concentration), more preferably 25 to 90 wt. %, even more preferably 30 to 80 wt. %, yet more preferably 40 to 80 wt %, still more preferably 50 to 80 wt. %, again more preferably 60 to 80 wt %, further preferably 70 to 80 wt. %, of the total of the water-absorbing agent and the hydrophilic fibers. If the core concentration is less than 20 wt. %, the amount of the water-absorbing agent used may be too small to impart sufficient heat retention to the whole diaper, which is not desirable.

If the absorbent in accordance with the present invention is manufactured from a water-absorbing agent and hydrophilic fibers, the method of manufacturing is not limited in any particular manner. For example, they are manufactured by dry-mixing a water-absorbing resin with hydrophilic fibers in a mixer or like mixing machine in such a ratio as to achieve the aforementioned core concentration and molding the resultant mixture into a web shape by, for example, air paper making.

Alternatively, water, an aqueous liquid, or one of various organic solvent is either sprayed or added dropwise to the mixture obtained from the dry mixing. The absorbent is preferably compress molded to a density of 0.001 to 0.50 g/cc and a basic weight of 0.01 to 0.20 g/cm$^2$.

Method of Manufacturing Absorbent Article

As mentioned above, the absorbent article in accordance with the present invention is made of an absorbent in accordance with the present invention, a liquid-permeable top sheet, and a liquid-impermeable back sheet.

The method of manufacturing of an absorbent article in accordance with the present invention is not limited in any particular manner. For example, the absorbent is sandwiched between a liquid-permeable base material (top sheet) and a liquid-impermeable base material (back sheet) and where necessary, provided with an elasticity member, a diffusion layer, adhesive tape, etc. to form an absorbent article, for example, an adult disposable diaper or a sanitary napkin.

The water-absorbing resin (or water-absorbing agent), absorbent, etc. in accordance with the present invention are able to give a heat retention property to absorbent articles and exhibit excellent heat retention and absorption properties over an extended period of time. Specific examples of such absorbent articles include, but not limited in any particular manner to, adult disposable diapers, baby diapers, sanitary napkins, so-called incontinence pads, and other hygiene materials of which the market is rapidly growing lately. The water-absorbing agent, absorbent, etc. in the absorbent article has an excellent heat retention property and low seepage, providing an excellent dry feel, and therefore greatly alleviates wearers' problems.

EXAMPLES

The following will present examples and comparative examples in accordance with the present inventions in a specific manner. The present invention is however by no means limited by the examples.

The capabilities of water-absorbing agents (or water-absorbing resins) and absorbent articles were measured as follows. Note that the water-absorbing agents (or water-absorbing resins) and absorbent articles were used at 25° C.±2° C./50% RH unless otherwise mentioned.

Water Content Ratio

A water ratio indicates the ratio of the water content in the water-absorbing resin (or water-absorbing agent). The relationship between the water content and the solid ratio is given by:

Water content ratio (wt. %)=100−Solid ratio (wt. %)

The water content ratio was measured as follows.

About 1 g of dry water-absorbing resin powder as well as the same, but wet, resin powder (total weight, $W_1$ was placed in an aluminum cup (weight $W_0$) having a bottom diameter of about 5 cm. The cup was left and dried in a 180° C., windless drier for 3 hours. After the drying, the weight, $W_2$, of the aluminum cup and water-absorbing resin was measured. The water content ratio was calculated by the formula:

Water content ratio(wt. %)=(1−($W_2$−$W_0$)/$W_1$)×100

Amount of Soluble Component (Water-Soluble Component)

184.3 g of a 0.90 wt. % aqueous solution of sodium chloride (physiological saline) was placed in a lidded plastic container with a capacity of 250 ml. To that aqueous solution, 1.00 g of a water-absorbing resin (or water-absorbing agent) was added and stirred for 1.6 hours to extract the soluble component from the resin. The extract liquid was filtered through filter paper (available from Toyo Roshi Kaisha, Ltd.; No. 2). 50.0 g of the filtered liquid was put aside for measurement.

First, an 0.1 N aqueous solution of sodium hydroxide was added dropwise to physiological saline per se to pH 10. Thereafter, a 0.1 N hydrochloric acid was added dropwise to pH 2.7, so as to determine blank titer ([bNaOH] ml, [bHCl] ml).

The same titration was done with respect to the filtered liquid to determine a titer ([NaOH] ml, [HCl] ml).

For example, for a water-absorbing resin made of a known amount of acrylic acid and its sodium salt, the amount of the soluble component in the water-absorbing resin is calculated from the average molecular weight of the monomer and the titer determined by the titration by the following formula:

Soluble component(wt. %)=0.1*(Average molecular weight)*184.3*100*([HCl]−[bHCl])/1000/1.00/50.0

If amount of acrylic acid and its sodium salt is unknown, the average molecular weight of the monomer is calculated from the neutrality ratio determined by the titration.

Centrifuge Retention Capacity (CRC) in 0.90 wt. % Aqueous Solution of Sodium Chloride (Physiological Saline)

0.20 g of a water-absorbing resin (or water-absorbing agent) was placed uniformly in an nonwoven cloth bag (60 mm×85 mm). The bag was soaked at 25±2° C. in a 0.90 wt. % aqueous solution of sodium chloride (physiological saline). After 30 minutes, the bag was pulled out of the solution and placed in a centrifugal separator under 250 G for 3 minutes to remove water. Then the bag weighed (=$W_1$ (g)). The same operation was done without involving a water-absorbing resin (or water-absorbing agent) and weighed ($W_0$ (g)). The centrifuge retention capacity (g/g) was calculated from $W_1$ and $W_0$ by the following formula:

Centrifuge retention capacity in 90 wt. % aqueous solution of sodium chloride (physiological saline) (g/g)={(Weight $W_1$ (g)−Weight $W_0$ (g))/Weight of water-absorbing resin (or water-absorbing agent) (g)}−1

Absorbency in 0.90 wt. % Aqueous Solution of Sodium Chloride (Physiological Saline) Against a Pressure of 2.0 kPa (AAP 0.3 Psi)

0.90 g of a water-absorbing agent (or water-absorbing resin) was uniformly sprinkled on a stainless net with 38 µm openings welded to an end (bottom) of a plastic support cylinder with an inner diameter of 60 mm. On that agent (resin) was placed a piston (cover plate) with an outer diameter of slightly less than 60 mm so that the piston did not leave any gap with the wall of the support cylinder and could move freely in vertical directions. The total weight $W_3$ (g) of the support cylinder, water-absorbing agent (or water-absorbing resin), and piston was measured. A load was then placed on the piston so that the water-absorbing agent (or water-absorbing resin) was under a uniform load of 2.0 kPa (ca. 0.3 psi) including the piston. A measuring device was thus set up. A glass filter measuring 90 mm in diameter and 5 mm in thickness was placed inside a petri dish with a diameter of 150 mm. A 0.90 wt. % aqueous solution of sodium chloride (physiological saline) at 25±2° C. was added so that it was flush with the top surface of the glass filter. On top of that was placed a piece of filter paper having a diameter of 90 mm (available from Toyo Roshi Kaisha, Ltd.; No. 2) so that the entire surface became wet. Excessive liquid was removed.

The measuring device was placed on the wet filter paper so that the device could absorb the liquid against pressure. As the liquid level fell below the top of the glass filter, the liquid was added to maintain the liquid level. After 60 minutes, the measuring device was lifted. The weight $W_4$ (g) of the support cylinder, swollen water-absorbing agent (or water-absorbing resin), and piston with the load removed was measured again. The absorbency in a 0.90 wt. % aqueous solution of sodium chloride (physiological saline) against a pressure of 2.0 kPa (g/g) was calculated from these weights $W_3$, $W_4$ by the following formula.

Absorbency in 0.90 wt. % aqueous solution of sodium chloride (physiological saline) against a pressure of 2.0 kPa (g/g)=(Weight $W_4$ (g)–Weight $W_3$ (g))/ Weight (g) of water-absorbing agent (or water-absorbing resin)

Mass-Average Particle Diameter (D50) and Standard Deviation of Logarithm ($\sigma\zeta$)

A water-absorbing agent (or water-absorbing resin) was sieve using 850 μm, 710 μm, 600 μm, 500 μm, 425 μm, 300 μm, 212 μm, 150 μm, 106 μm, 75 μm, 45 μm, and other JIS standard sieves. The percentages (R) of residuals were plotted on logarithmic probability paper. The mass-average particle diameter (D50) was read from the plots. The standard deviation of logarithm ($\sigma\zeta$) is given by:

$$\sigma\zeta = 0.5 \times \ln(X_2/X_1)$$

where $X_1$, $X_2$ represent a particle diameter when R=84.1% and R=15.9% respectively. The smaller the $\sigma\zeta$, the narrower the particle size distribution.

The sieving was done as follows. 10.00 g of water-absorbing agent (or water-absorbing resin) was introduced to JIS standard sieves (Iida testing sieves, inner diameter of 80 mm) with openings measuring 850 μm, 710 μm, 600 μm, 500 μm, 425 μm, 300 μm, 212 μm, 150 μm, 106 μm, 75 μm, 45 μm, etc. and classify for 5 minutes in a Ro-tap sieve shaker (available from Iida Seisakusho, Co., Ltd., ES-65 sieve shaker) for classification. The mass-average particle diameter (D50), as described in U.S. Pat. No. 5,051,259 and other documents, indicates a particle diameter which corresponds to 50 wt. % of all particles using a standard sieve with openings of the same size.

Saline Flow Conductivity (SFC) for 0.69 wt. % Aqueous Solution of Sodium Chloride The saline flow conductivity (SFC) for a 0.69 wt. % aqueous solution of sodium chloride was measured as described in the published Japanese translation of a PCT application Tokuhyohei 9-51.0889 (see page 82, "F. Test methods, 1. Saline flow conductivity (SFC) test") (U.S. Pat. No. 5,599,335).

Heat Retention Indicator for Water-Absorbing Resin

Heat Retention Indicator 1

Figure 1:
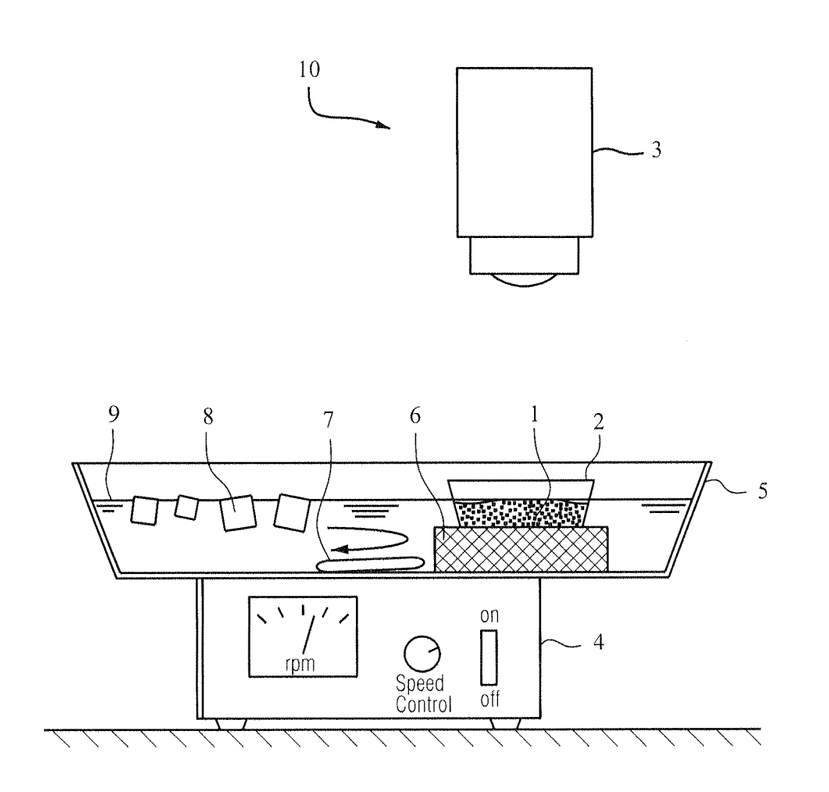
FIG. 1 is a schematic of the configuration of a measuring device for a heat retention indicator, one of capabilities of the water-absorbing agent of the present invention.

FIG. 1 is a schematic of the arrangement of a measuring device 10. Using this device is measured the heat retention indicator, an indicator of performance of the water-absorbing agent in accordance with the present invention. As shown in FIG. 1, the measuring device 10 includes an aluminum cup 2, a thermography 3, and an ice-water bath 5 (2400 ml).

In a windless, 24±1° C./RH50% room where there was no air flow, 2.0 g of a water-absorbing agent (or water-absorbing resin) was placed in an aluminum cup (foil container, product no. 107, available from Toyo Ekco Inc.) 2. The container 2 measured about 5 cm in bottom diameter, about 2 cm in height, 0.05 mm in bottom thickness, and 0.16 to 0.25 mm in side face thickness, and weighed about 0.83 g. Then, 20 ml of a 0.90 wt. % aqueous solution of sodium chloride (physiological saline) heated to 50° C. was quickly poured in and let swell for 2 minutes so that: the gel layer became even. After the swell, the gel layer 1 was about 1 cm high.

Next, the swollen gel was moved quickly, preferably in 3 seconds, into the 3° C. ice-water bath 5 (2400 ml) containing ice 8 and water 9. At the same time, the recording of the surface temperature of the swollen gel layer 1 at the center of its top surface was started. Using the thermography (Neo Thermo, available from Nippon Avionics Co., Ltd.) 3, the temperature was continuously recorded for 20 minutes after the start of the cooling. During the temperature recording, the ice-water bath 5 was maintained at 3° C. by stirring with a stirring bar 7 controlled by a stirring device 4. The aluminum cup 2 had to be immersed in the ice-water bath 5 at least up to the level flush with the top of the gel layer 1 (about 1 cm). The height of the aluminum cup 2 may be adjusted, for example, using an adjuster table 6 which includes preferably a mesh structure in consideration of the temperature of the aluminum cup 2.

After observing the gel layer surface temperature for 20 minutes after the start of the cooling, the recorded gel layer Surface temperature was plotted in a graph with 1 minute intervals. The X axis indicated the time with 0 minutes being the start of the cooling and 20 minutes being the end of the recording. The Y axis indicated the temperature. A change in gel surface temperature per minute was calculated between 5 minutes and 10 minutes into the cooling (temperature changes between 5 and 6 minutes, 6 and 7 minutes, 7 and 8 minutes, 8 and 9 minutes, 9 and 10 minutes into the cooling). The greatest of the absolute values of the changes was picked up as the heat retention indicator 1.

Heat Retention Indicator 2

The heat retention indicator 2 was measured during the cooling for the heat retention indicator 1. The heat retention indicator 2 is the surface temperature of the swollen gel 10 minutes into the cooling.

Heat Retention Indicator 3

The heat retention indicator 3 was measured during the cooling for the heat retention indicator 1. The heat retention indicator 3 is the time (seconds) taken by the surface temperature of the swollen gel to reach 37° C. after the start of the cooling.

User Test

Ten healthy adults wore a diaper (absorbent article) having a 70 wt. % core concentration so that the diaper well fitted the body of the wearer. 150 ml of a 0.90 wt. % aqueous solution of sodium chloride (physiological saline) heated up to 37° C. was injected through a syringe over about 1 minute. The cold feel was evaluated on a scale of one to five 15 minutes and 30 minutes after the injection, with level 1 for "uncomfortable," level 2 for "a little uncomfortable," level 3 for "neither comfortable nor uncomfortable," level 4 for "a little comfortable," and level 5 for "comfortable." Evaluation was done in terms of the average value of the results.

Reference Example 1

Preparation/Neutral Polymerization of Water-Absorbing Resin (a)

5.98 g of polyethylene glycol diacrylate (n=9) was dissolved in 6600 g of an aqueous solution of sodium acrylate having a neutrality ratio of 68 mole % (concentration of monomer: 37.7 wt. %) in a reactor to prepare a reaction liquid. The reactor was a lidded stainless double-arm kneader with two sigma-type blades and a jacket. The inner capacity of the rector was 10 liters. Next, the reaction liquid was subjected to nitrogen replacement under a nitrogen gas atmosphere for 20 minutes. Subsequently, 35.8 g of a 10 wt. % aqueous solution of sodium persulfate and 1.49 g of a 1 wt. % aqueous solution of L-ascorbic acid were added to the reaction liquid while stirring, about 20 seconds after which polymerization started. Polymerization was carried out at 20 to 95° C. while crushing the generated gel. A crosslinked polymer in water-containing gel form was obtained 42 minutes into the polymerization. The obtained crosslinked polymer in water-containing gel form was divided into pieces, each measuring about 5 mm or less in diameter. The crosslinked polymer in water-containing gel form divided into pieces was spread on a 20 mesh (850 μm openings) net and hot-air-dried under heat at 180° C. for 40 minutes. Next, the polymer was crushed in a roll mill and classified using JIS standard sieves with 850 μm and 150 μm openings to prepare a water-absorbing resin (a) of a pulverized irregularly pulverized. The resin (a) had a mass average particle diameter of 450 μm, contained 28 wt. % particles measuring from 850 to 600 μm in diameter and 2 wt. % particles measuring less than 150 μm in diameter, and had a standard deviation of logarithm (σζ) of 0.364 and a water content ratio of 6 wt. %.

Physical properties of the obtained water-absorbing resin (a) were measured. The CRC was 42.6 (g/g). The amount of the soluble component was 12.5 wt. %.

Reference Example 2

Preparation/Neutral Polymerization of Water-Absorbing Resin (b)

A water-absorbing resin (b) of an irregularly pulverized shape was prepared by the same operation as with reference example 1, except that the concentration of monomer was changed to 40 wt. %, the neutrality ratio was changed to 75 mole %, and the crosslinking agent was changed to 3.97 g of trimethylolpropane triacrylate. The resin (b) had a mass average particle diameter of 450 μm, contained 28 wt. % particles measuring from 850 to 600 μm in diameter and 2 wt. % particles measuring less than 150 μm in diameter, and had a standard deviation of logarithm (σζ) of 0.364 and a water content ratio of 6 wt. %.

Physical properties of the obtained water-absorbing resin (b) were measured. The CRC was 37.6 (g/g). The amount of the soluble component was 12.3 wt. %.

Example 1

Water-Absorbing Agent 500 g of the water-absorbing resin (a) obtained in reference example 1 was placed in a 5 liter Loedige mixer (M5R, available from Loedige, Co.). Then, 22.5 g of a solution of glycerine/water/isopropyl alcohol mixed at 0.75/3/0.75 (wt. %) was introduced by spraying with a sprayer and mixed for 1 minute, while rotating the major axis (plow-shaped blade) of the Loedige mixer at 330 rpm.

Thereafter, the stirring was stopped, and the resultant mixture was quickly removed.

Next, the obtained mixture was introduced into a 5 liter mortar mixer (available from Nishi Nihon Shikenki Seisakusho K.K.) in which the container was heated in an oil bath at 210° C. The mixture was then stirred and mixed so as to uniformly receive heat. About 20 minutes later, the mixture was removed from the mortar mixer. The entire mixture was then passed through a 850 μm JIS standard sieve and subjected to surface crosslinking.

480 g of the surface crosslink mixture was placed again in a 5 liter Loedige mixer (M5R, available from Loedige, Co.). Then, 9.6 g of water was introduced by spraying with a sprayer and mixed for 1 minute, while rotating the major axis (plow-shaped blade) of the Loedige mixer at 330 rpm, to obtain a water-containing product.

The obtained water-containing product was moved to a sealed container. The product was thermally cured at 60° C. in a windless drier for 1 hour (to cause the water content added inside the water-containing product to be absorbed). After 1 hour, the water-containing product was removed from the drier. The entire product was passed through a 850 μm JIS standard sieve to obtain a water-absorbing agent (1).

The CRC, AAP 0.3 psi, mass-average particle diameter (D 50), standard deviation of logarithm of particle size distribution, SFC, heat retention indicator 1, heat retention indicator 2, and heat retention indicator 3 of the obtained water-absorbing agent (1) were measured. Results are shown in Table 1 below.

Example 2

Water-Absorbing Agent

A water-absorbing agent (2) was prepared by adding Aerosil 200 (available from Aerosil) to the water-absorbing agent (1) obtained in example 1 at 0.30 wt. %. The obtained water-absorbing agent (2) was evaluated similarly to example 1 Results are summarized in Table 1 below.

Example 3

Water-Absorbing Agent 500 g of the water-absorbing resin (b) obtained in reference example 2 was put in a 5 liter Loedige mixer (M5R, available from Loedige, Co.). Then, 11.25 g of a solution of glycerine/water mixed at 0.75/1.5 (wt. %) was introduced by spraying with a sprayer and mixed for 1 minute, while rotating the major axis (plow-shaped blade) of the Loedige mixer at 330 rpm. Thereafter, the stirring was stopped, and the resultant mixture was quickly removed.

Next, the obtained mixture was introduced into a 5 liter mortar mixer (available from Nishi Nihon Shikenki Seisakusho K.K.) in which the container was heated in an oil bath at 205° C. The mixture was then stirred and mixed so as to uniformly receive heat. About 40 minutes later, the mixture was removed from the mortar mixer. The entire mixture, was then passed through a 850 μm JIS standard sieve and subjected, to surface crosslinking.

480 g of the surface crosslink mixture was placed again in a 5 liter Loedige mixer (M5R, available from Loedige, Co.). Then, 9.6 g of water was introduced by spraying with a sprayer and mixed for 1 minute, while rotating the major axis (plow-shaped blade) of the Loedige mixer at 330 rpm, to obtain a water-containing product.

The obtained water-containing product was moved to a sealed container. The product was thermally cured at 60° C. in a windless drier for 1 hour (to cause the water content added inside the water-containing product to be absorbed). After 1 hour, the water-containing product was removed from the drier. The entire product was passed through a 850 μm JIS standard sieve to obtain a water-containing powder.

A water-absorbing agent (3) was prepared by adding Aerosil 200 (available from Aerosil) to the obtained water-containing powder at 0.30 wt. %.

The obtained water-absorbing agent (3) was evaluated similarly to example 1. Results are summarized in Table 1 below.

Comparative Example 1

Water-Absorbing Agent

The water-absorbing resin (a) obtained in reference example 1 was designated as a comparative water-absorbing agent (4) and evaluated similarly to example 1. Results are summarized in Table 1.

Comparative Example 2

Water-Absorbing Agent

The water-absorbing agent (1) obtained in example 1 was further classified using JIS standard sieves for particles measuring 300 to 150 μm. The obtained particles were designated as a comparative water-absorbing agent (5) and evaluated similarly to example 1. Results are summarized in Table 1.

Comparative Example 3

Water-Absorbing Agent 500 g of the water-absorbing resin (a) obtained in reference example 1 was placed in a 5 liter Loedige mixer (M5R, available from Loedige, Co.). Then, 28.0 g of a solution of 1,4-butanediol/propylene glycol/water mixed at 0.3/0.5/3.0 (wt. %) was introduced by spraying with a sprayer and mixed for 1 minute, while rotating the major axis (plow-shaped blade) of the Loedige mixer at 330 rpm.

Thereafter, the stirring was stopped, and the resultant mixture was quickly removed.

Next, the obtained mixture was introduced into a 5 liter mortar mixer (available from Nishi Nihon Shikenki Seisakusho K.K.) in which the container was heated in an oil bath at 200° C. The mixture was then stirred and mixed so as to uniformly receive heat. About 40 minutes later, the mixture was removed from the mortar mixer. The entire mixture was then passed through a 850 μm JIS standard sieve and subjected to surface crosslinking.

480 g of the surface crosslink mixture was placed again in a 5 liter Loedige mixer (M5R, available from Loedige, Co.). Then, 9.6 g of water was introduced by spraying with a sprayer and mixed for 1 minute, while rotating the major axis (plow-shaped blade) of the Loedige mixer at as high as 330 rpm, to obtain a water-containing product.

The obtained water-containing product was moved to a sealed container. The product was thermally cured at 60° C. in a windless drier for 1 hour (to cause the water content added inside the water-containing product to be absorbed). After 1 hour, the water-containing product was removed from the drier. The entire product was passed through a 850 μm JIS standard sieve to obtain a comparative water-absorbing agent (6).

The obtained comparative water-absorbing agent (6) was evaluated similarly to example 1. Results are summarized in Table 1.

Comparative Example 4

Water-Absorbing Agent 1.18 g (0.04 mole %) of trimethylolpropane triacrylate was dissolved in 720 g of acrylic acid in a reactor to prepare a reaction liquid. The reactor was a lidded stainless double-arm kneader with sigma-type blades and a jacket. The inner capacity of the reactor was 10 liters. Next, the reaction liquid was subjected to nitrogen replacement under a nitrogen gas atmosphere for 20 minutes. Subsequently, 21.6 g of a 10 wt. % aqueous solution of 2,2'-azobis(2-amidinopropane)dihydrochloride, 18.0 g of a 1 wt. % aqueous solution of L-ascorbic acid, and 20.6 g of a 3.5 wt. % aqueous solution of hydrogen peroxide were added to the reaction liquid while stirring to initiate polymerization. The stirring was stopped upon the initiation of polymerization. After the temperature of the reaction liquid rose to a peak, the reaction liquid was maintained at 55° C. or higher for 3 hours for aging. After the end of the reaction, the generated gel was crushed by rotating the blades to obtain a crosslinked polymer in water-containing gel form.

Next, while the crosslinked polymer in water-containing gel form was being further crushed by rotating the blades, the crosslinked polymer was maintained at about 50° C. and mixed with 700 g of an 40 wt. % aqueous solution of sodium hydroxide as a neutralizer which was added dropwise over 40 minutes. Thereafter, the blades were stopped, and the polymer was maintained at 50° C. for 80 minutes. Then, 400 g of deionized water was added to the polymer, mixed, and left at room temperature for 24 hours to complete neutralization (neutrality ratio=70 mole %).

Subsequently, the neutralized crosslinked polymer in water-containing gel form was spread on a 20 mesh (850 μm openings) net and hot-air-dried under heat at 160° C. for 40 minutes. Next, the polymer was pulverized in a roll mill and classified using a JIS standard sieve with 850 μm openings to prepare a water-absorbing resin (c) of an irregularly pulverized shape. The resin (c) had a mass average particle diameter of 405 μm, contained 20 wt. % particles measuring from 850 to 600 μm in diameter and 12 wt. % particles measuring less than 150 μm in diameter, and had a standard deviation of logarithm (σζ) of 0.520 and a water content ratio of 6 wt. %.

Physical properties of the obtained water-absorbing resin (c) were measured. The CRC was 38.1 (g/g). The amount of the soluble component was 9.8 wt. %.

Subsequently, 500 g of the obtained water-absorbing resin (c) was placed in a 5 liter Loedige mixer (M5R, available from Loedige, Co.). Then, 16.0 g of a solution of 1,3-dioxolane-2-on/water/ethanol mixed at 0.2/1.0/2.0 (wt. %) was introduced by spraying with a sprayer and mixed for 1 minute, while rotating the major axis (plow-shaped blade) of the Loedige mixer at as high as 330 rpm.

Thereafter, the stirring was stopped, and the resultant mixture was quickly removed.

Next, the obtained mixture was introduced into a 5 liter mortar mixer (available from Nishi Nihon Shikenki Seisakusho K.K.) in which the container was heated in an oil bath at 180° C. The mixture was then stirred and mixed so as to uniformly receive heat. About 60 minutes later, the mixture was removed from the mortar mixer. The entire mixture was then passed through a 850 μm JIS standard sieve to obtain a comparative water-absorbing agent (7).

The obtained comparative water-absorbing agent (7) was evaluated similarly to example 1. Results are shown in Table 1 below.

Comparative Example 5

Water-Absorbing Agent

A water-absorbing resin (d) of a irregularly pulverized shape was prepared by the same operation as with reference example 1, except that the concentration of monomer was changed to 40 wt. %, the neutrality ratio was changed to 75 mole %, and the crosslinking agent was changed to 4.54 g of polyethylene glycol diacrylate (n=9). The resin (d) had a mass average particle diameter of 395 μm, contained 5 wt. % particles measuring less than 150 μm in diameter, and had a standard deviation of logarithm (σζ) of 0.363 and a water content ratio of 6 wt. %.

Physical properties of the obtained water-absorbing resin (d) were measured. The CRC was 47.0 (g/g). The amount of the soluble component was 20.0 wt. %.

500 g of the obtained water-absorbing resin (d) was placed in a 5 liter Loedige mixer (M5R, available from Loedige, Co.). Then, 25.2 g of a solution of diethylene glycol diglycidyl ether/propylene glycol/water/isopropyl alcohol mixed at 0.03/1/3/1 (wt. %) was introduced by spraying with a sprayer and mixed for 1 minute, while rotating the major axis (plow-shaped blade) of the Loedige mixer at 330 rpm.

Thereafter, the stirring was stopped, and the resultant mixture was quickly removed.

Next, the obtained mixture was introduced into a 5 liter mortar mixer (available from Nishi Nihon Shikenki Seisakusho K.K.) in which the container was heated in an oil bath at 210° C. The mixture was then stirred and mixed so as to uniformly receive heat. About 40 minutes later, the mixture was removed from the mortar mixer. The entire mixture was then passed through a 850 μm JIS standard sieve and subjected to surface crosslinking.

480 g of the surface crosslinked mixture was placed again in a 5 liter Loedige mixer (M5R, available from Loedige, Co.). Then, 9.6 g of water was introduced by spraying with a sprayer and mixed for 1 minute, while rotating the major axis (plow-shaped blade) of the Loedige mixer at 330 rpm, to obtain a water-containing product.

The obtained water-containing product was moved to a sealed container. The product was thermally cured at 60° C. in a windless drier for 1 hour (to cause the water content added inside the water-containing product to be absorbed). After 1 hour, the water-containing product was removed from the drier. The entire product was passed through a 850 μm JIS standard sieve to obtain a comparative water-absorbing agent (8).

The obtained comparative water-absorbing agent (8) Was evaluated similarly to example 1. Results are summarized in Table 1 below.

Comparative Example 6

Water-Absorbing Agent

The water-absorbing agent obtained in example 10 of Japanese published patent application 2001-98170 (Tokukai 2001-98170) (U.S. Pat. No. 6,586,549) was evaluated similarly to example 1. Results are summarized in Table 1. This water-absorbing agent was designated as a comparative water-absorbing agent (9).

Comparative Example 7

Water-Absorbing Agent

The water-absorbing agent obtained in example 1 of Japanese published patent application 2002-45395 (Tokukai 2002-45395) (U.S. Pat. No. 6,617,489) was evaluated similarly to example 1. Results are summarized in Table 1. This water-absorbing agent was designated as a comparative water-absorbing agent (10).

Comparative Example 8

Water-Absorbing Agent

The water-absorbing agent obtained in example 3 of Japanese published patent application 2002-45395 (Tokukai 2002-45395) (U.S. Pat. No. 6,617,489) was evaluated similarly to example 1. Results are summarized in Table 1. This water-absorbing agent was designated as a comparative water-absorbing agent (11).

Comparative Example 9

Water-Absorbing Agent

The water-absorbing agent obtained in comparative example 2 of Japanese published patent application 2002-45395 (Tokukai 2002-45395) (U.S. Pat. No. 6,617,489) was evaluated similarly to example 1. Results are summarized in Table 1. This water-absorbing agent was designated as a comparative water-absorbing agent (12).

Example 4

Absorbent Article 70 weight parts of the water-absorbing agent (1) obtained in example 1 was dry mixed with 30 weight parts with crushed wood pulp in a mixer. Next, the obtained mixture was subjected to a batch-type air paper making machine to form a web measuring a 130 mm×400 mm on a 400 mesh (38 μm openings) wire screen. Further, the web was pressed for 5 seconds under a load of 196.14 kPa to obtain an absorbent having a basic weight of about 0.05 g/cm².

Subsequently, an absorbent article, that is, a pad type of adult disposable diaper (1) was made by combining a so-called back sheet (liquid-impermeable sheet) which was made of a liquid-impermeable polypropylene, the foregoing absorbent, and a top sheet (liquid-permeable sheet) which is an nonwoven cloth made of a liquid-permeable polypropylene in this order using a double-sided adhesive tape. The absorbent article (1) weighed 50 g.

A user test was conducted on the obtained absorbent article (1) Results are summarized in Table 2.

Example 5

Absorbent Article

An absorbent article (2) was made by replacing the water-absorbing agent (1) used in example 4 with the water-absorbing agent (2) obtained in example 2.

A user test was conducted on the obtained absorbent article (2). Results are summarized in Table 2.

Example 6

Absorbent Article

An absorbent article (3) was made by replacing the water-absorbing agent (1) used in example 4 with the water-absorbing agent (3) obtained in example 3.

A user test was conducted on the obtained absorbent article (3). Results are summarized in Table 2.

Comparative Examples 10 to 18

Absorbent Articles

Comparative absorbent articles (1) to (9) were made by replacing the water-absorbing agent (1) used in example 4 with the comparative water-absorbing agents (4) to (12) obtained in comparative examples 1 to 9.

A user test was conducted on the obtained comparative absorbent articles (1) to (9). Results are summarized in Table 2.

excellent heat retention and absorption, providing a very excellent water absorber in comparison with conventional absorbents. An absorbent article in which the water-absorbing agent obtained according to the present invention is used has excellent heat retention and absorption, easing discomfort felt by the consumer in the absorbent article.

Therefore, the water-absorbing agent in accordance with the present invention can find a wide variety of applications, such as moisture absorbing agents, dehumidifying agents, and building materials. Especially, the water-absorbing agent is preferably used as hygiene materials absorbing feces, urine, and blood, typical examples of which include paper diapers and sanitary napkins.

TABLE 1

|  |  | CRC (g/g) | AAP 0.3 (g/g) | D50 (μm) | σζ | SFC*) | H.R.I. 1 (° C./min) | H.R.I. 2 (° C.) | H.R.I 3 (Second) |
|---|---|---|---|---|---|---|---|---|---|
| Ex. 1 | w.a. agent (1) | 31 | 27 | 500 | 0.324 | 6.4 | 2.9 | 22 | 150 |
| Ex. 2 | w.a. agent (2) | 31 | 25 | 535 | 0.360 | 3.5 | 2.7 | 24 | 162 |
| Ex. 3 | w.a. agent (3) | 31 | 25 | 484 | 0.333 | 3.5 | 2.2 | 23 | 144 |
| C. ex. 1 | C. w.a. agent (4) | 38 | 8 | 450 | 0.364 | 0 | 3.3 | 11 | 60 |
| C. ex. 2 | C. w.a. agent (5) | 31 | 25 | 200 | 0.134 | 0 | 4.0 | 16 | 108 |
| C. ex. 3 | C. w.a. agent (6) | 34 | 32 | 471 | 0.340 | 10 | 3.2 | 19 | 120 |
| C. ex. 4 | C. w.a. agent (7) | 31 | 25 | 435 | 0.510 | 15 | 3.6 | 15 | 114 |
| C. ex. 5 | C. w.a. agent (8) | 34 | 31 | 395 | 0.363 |  | 3.5 | 15 | 120 |
| C. ex. 6 | C. w.a. agent (9) | 42 | 23 | 450 | 0.343 |  | 3.2 | 17 | 135 |
| C. ex. 7 | C. w.a. agent (10) | 36 | 34 | 450 | 0.343 | 3 | 4.8 | 13 | 120 |
| C. ex. 8 | C. w.a. agent (11) | 34 | 32 | 550 | 0.390 | 30 | 3.3 | 17 | 120 |
| C. ex. 9 | C. w.a. agent (12) | 28 | 30 | 430 | 0.390 | 35 | 3.4 | 19 | 168 |

*)($\times 10^{-7}$ cm$^3$sec/g)
*)In embodiments 1 to 3, particles measuring 600 μm to 300 μm account for 60 wt. % to 90 wt. %. Particles less than 150 μm account for less than 3 wt. %.

TABLE 2

|  |  | Evaluation by user | Condition after absorbing liquid |
|---|---|---|---|
| Example 4 | Absorbent article (1) | 4.0 | No Leak |
| Example 5 | Absorbent article (2) | 4.2 | No Leak |
| Example 6 | Absorbent article (3) | 4.5 | No Leak |
| C. ex. 10 | C. absorbent article (1) | 1.0 | Leaks, wet |
| C. ex. 11 | C. absorbent article (2) | 1.5 | Leaks, wet |
| C. ex. 12 | C. absorbent article (3) | 3.0 | No Leak |
| C. ex. 13 | C. absorbent article (4) | 2.4 | Leaks |
| C. ex. 14 | C. absorbent article (5) | 3.0 | No Leak |
| C. ex. 15 | C. absorbent article (6) | 1.5 | Leaks, wet |
| C. ex. 16 | C. absorbent article (7) | 3.0 | No Leak |
| C. ex. 17 | C. absorbent article (8) | 2.4 | Leaks |
| C. ex. 18 | C. absorbent article (9) | 2.4 | Leaks |

C. ex.: Comparative example,
C. absorbent article: Comparative absorbent article
Evaluation levels
1: Uncomfortable
2: A little uncomfortable
3: Not comfortable, not uncomfortable
4: A little comfortable
5: Comfortable The embodiments and examples described in Best Mode for Carrying Out the Invention are for illustrative purposes only and by no means limit the scope of the present invention. Variations are not to be regarded as a departure from the spirit and scope of the invention, and all such modifications as would be obvious to one skilled in the art are intended to be included within the scope of the claims below.

INDUSTRIAL APPLICABILITY

The water-absorbing agent obtained in the present invention, when applied as a water absorber in diapers, exhibits

The invention claimed is:

1. A water-absorbing agent, comprising 90 wt. % or more of a water-absorbing resin including a partially neutralized polymer of polyacrylic acid, the partially neutralized polymer having a crosslinking structure constructed by polymerization of an acrylic acid (salt) (a monomer other than the acrylic acid (salt) is 0 to 30 mole % relative to the acrylic acid (salt)), wherein
   the water-absorbing agent is surface-treated, and
   the water-absorbing resin contains 10 to 40 mole % of acrylic acid and 90 to 60 mole % of acrylate (the sum should be 100 mole %), and salt-forming neutralization of the water-absorbing resin is (i) performed before polymerization while the water-absorbing resin is in monomer form, or (ii) performed during or after polymerization while the water-absorbing resin is in polymer form, or (iii) performed by a combination of (i) and (ii),
   the water-absorbing agent contains (iv) polyhydric alcohol containing 2 to 10 carbons per molecule or (v) water-insoluble inorganic fine particles,
   the water-absorbing agent meets all of properties (1) through (4):
   (1) heat retention indicator 1 (maximum temperature decrease per minute 5 to 10 minutes after 10 times swelling in a 0.90 wt. % sodium chloride at 50° C.) is from 0 to 3.0° C./min;
   (2) a centrifuge retention capacity in a 0.90 wt. % aqueous solution of sodium chloride (30 minute value) is 34 g/g or less;
   (3) an absorbency in a 0.90 wt. % aqueous solution of sodium chloride against a pressure of 2.0 kPa (60 minute value) is less than 30 g/g; and
   (4) a saline flow conductivity (SFC) for a 0.69 wt. % aqueous solution of sodium chloride is less than $20 \times 10^{-7}$ cm$^3$ sec/g, wherein the water-absorbing agent is particles,
the water-absorbing agent meets following conditions:
particles having diameters from 600 to 300 μm as specified by sieve classification account for 60 wt. % or more, and those less than 150 μm account for 3 wt. % or less; and
a standard deviation of logarithm (G) of particle size distribution is from 0.250 to 0.400;
wherein a mass-average particle diameter (specified by sieve classification) is from 400 to 600 μm.

2. The water-absorbing agent as set forth in claim 1, further comprising water-insoluble inorganic fine particles, besides the water-absorbing resin.

3. The water-absorbing agent as set forth in claim 2 wherein the water-absorbing agent contains water-insoluble inorganic fine particles of 0.0001 to 10 wt. %.

4. The water-absorbing agent as set forth in claim 1, wherein a heat retention indicator 2 (gel surface temperature 10 minutes after 10 times swelling in a 0.90 wt. % sodium chloride at 50° C.) is 20° C. or higher.

5. The water-absorbing agent as set forth in claim 1, wherein a heat retention indicator 3 (time taken by a gel surface temperature to return to 37° C. after 10 times swelling in a 0.90 wt. % sodium chloride at 50° C.) is 120 seconds or longer.

6. The water-absorbing agent as set forth in claim 1, wherein a content of the polyhydric alcohol is 0.001 to 10 wt. % relative to the water-absorbing resin.

7. The water-absorbing agent as set forth in claim 1, wherein:
the polyhydric alcohol is selected from polyhydric alcohol compounds such as mono, di, tri, and tetra ethylene glycol, monopropylene glycol, 1,3-propanediol, dipropylene glycol, 2,3,4-trimethyl-1,3-pentanediol, glycerine, polyglycerine, 2-butene-1,4-diol, 1,4-butanediol, 1,3-butanediol, 1,5-pentanediol, 1,6-hexanediol, and 1,2-cyclohexanedimethanol.

8. The water-absorbing agent as set forth in claim 1, wherein:
a content of the water-insoluble inorganic fine particles is 0.0001 to 5 wt. % relative to the water-absorbing resin.

9. The water-absorbing agent as set forth in claim 1, wherein:
the surface crosslinking agent is selected from polyhydric alcohol compounds, epoxy compounds, polyamine compounds and their condensates with haloepoxy compounds, oxazoline compounds, mono, di, and polyoxazolidinone compounds, polyvalent metallic compounds, and alkylene carbonate compounds.

10. An absorbent, comprising the water-absorbing agent as set forth in claim 1 and hydrophilic fibers.

11. The absorbent as set forth in claim 10, wherein the water-absorbing agent accounts for 20 wt. % or more of a total of the water-absorbing agent and hydrophilic fibers.

12. An absorbent article, comprising the absorbent as set forth in claim 10; a liquid-permeable top sheet; and a liquid-impermeable back sheet.

* * * * *